United States Patent [19]

Stewart et al.

[11] 4,254,024

[45] Mar. 3, 1981

[54] TETRAPEPTIDES AND DERIVATIVES HAVING OPIATE ACTIVITY

[75] Inventors: John M. Stewart, Denver; Dan H. Morris, Broomfield, both of Colo.; Richard E. Chipkin, Bloomfield, N.J.

[73] Assignee: Pennwalt Corporation, Philadelphia, Pa.

[21] Appl. No.: 85,253

[22] Filed: Oct. 16, 1979

[51] Int. Cl.$^3$ ........................................... C07C 103/52
[52] U.S. Cl. ............................................. 260/112.5 R
[58] Field of Search .................. 424/177; 260/112.5 R

[56] References Cited

U.S. PATENT DOCUMENTS

| | | | |
|---|---|---|---|
| 4,127,534 | 11/1978 | Coy et al. | 424/177 |
| 4,127,535 | 11/1978 | Coy et al. | 424/177 |
| 4,178,371 | 12/1979 | Morgan | 424/177 |

FOREIGN PATENT DOCUMENTS

| | | | |
|---|---|---|---|
| 2741393 | 3/1978 | Fed. Rep. of Germany | 260/112.5 R |
| 1513768 | 10/1975 | United Kingdom | 260/112.5 R |

OTHER PUBLICATIONS

M. J. Geisow, et al., Nature, 269, (1977) 167, 168.
H. E. Bleich, et al., Biochem. and Biophys. Res. Commun., 71, (1976), 168–174.

Primary Examiner—Delbert R. Phillips
Attorney, Agent, or Firm—Allan R. Plumley; John S. Roberts, Jr.

[57] ABSTRACT

A class of tetrapeptides having opiate activity having the formula

H-Tyr-X-Y-Z wherein X is D-amino acid radical; Y is Phe, DPhe, MePhe, DMePhe, Trp or DTrp; Z is Met-OH, Met-ol, Met(O)-ol, Met-OR, Met-NH$_2$, MetHNR, DMet-OH, DMet-ol, DMet(O)-ol, DMet-OR, DMet-NH$_2$, DMetNHR, Leu-OH, Leu-ol, Leu-OR, Leu-NH$_2$, Leu-NHR, DLeu-OH, DLeu-ol, DLeu-OR, DLeu-NH$_2$ or DLeu-NHR, and R is C$_1$–C$_4$-alkyl or C$_1$–C$_4$-hydroxyalkyl, are disclosed.

11 Claims, No Drawings

TETRAPEPTIDES AND DERIVATIVES HAVING OPIATE ACTIVITY

BRIEF SUMMARY OF THE INVENTION

This invention relates to tetrapeptides and their derivatives which exhibit activity as opiates. It is known that certain pentapeptides and their derivatives have opiate activity. For example, methionine and leucine enkephalin possess some opiate activity and certain synthetic pentapeptides related to the enkephalins are much more potent opiates than the enkephalins. Surprisingly, we have found a class of tetrapeptides which are active opiates. The opiate activity of the tetrapeptides described here is particularly surprising in view of the MINIREVIEW by R. Friederickson, *Life Sciences*, Vol. 21, no. 1, Pergammon Press, 1977, pp. 23–42. In that MINIREVIEW it is reported at page 24 that certain tripetides and tetrapeptides related to the enkephalins have little or no pharmacological activity as measured by in vitro tests on guinea pig ileum. For example, $Met^5$ enkephalin in which either the 2 or 3 glycine is removed is reported to have less than 1% of the activity of the pentapeptides. In contrast, the tetrapeptides of this invention, which can be described as des-$Gly^3$ enkephalin analogs having the $Gly^2$ replaced, are nearly as active as $Met^5$ enkephalin and in some species more active.

PRIOR ART STATEMENT

U.S. Pat. No. 4,028,319, Jones et al
U.S. Pat. No. 4,062,835, Tinney.
D. Roemer et al, *Nature*, 268:547–550, Aug. 11, 1977.

DETAILED DESCRIPTION OF THE INVENTION

The compounds of this invention are denominated tetrapeptides although the terminal carbonyl group in most of the compounds disclosed has been converted to other functional groups such as the amide or the ester or reduced to the alcohol. These tetrapeptides have the formula H-Tyr-X-Y-Z wherein
X is a D-amino acid radical;
Y is Phe, DPhe, MePhe, DMePhe, Trp or DTrp;
Z is Met-OH, Met-ol, Met(O)-ol, Met-OR, Met-$NH_2$, Met-NHR, DMet-OH, DMet-ol, DMet(O)-ol, DMet-OR DMet-$NH_2$, DMet-NHR, Leu-OH, Leu-ol, Leu-OR, Leu-$NH_2$, Leu-NHR, DLeu-OH, DLeu-ol, DLeu-OR, DLeu-$NH_2$, or DLeu-NHR; and
R is $C_1$–$C_4$-alkyl or $C_1$–$C_4$- hydroxyalkyl.

The preferred tetrapeptide compounds are those of formula (I) wherein
X is DAla or DLys;
Y is Phe or DPhe; and
Z is Met-OH, Met-$NH_2$, Met-ol, Met-$OCH_3$, Met-$NHCH_3$, Met-$NHC_2H_5$, Met-NH-$(CH_2)_2$-OH, Met-(O)-ol, or Leu-$NH_2$.

The abbreviations used above are those commonly used in the nomenclature of peptides. The amino acids represented have the L-configuration unless otherwise indicated.

The tetrapeptides can be synthesized by known techniques such as described in Stewart and Young, *Solid Phase Peptide Synthesis*, W. H. Freeman and Company, San Francisco, 1969, which is incorporated hereby by reference, and also by classical solution phase techniques. Synthetic routes suitable for several of the tetrapeptides of this invention are described in the working examples below.

In the preparation of tetrapeptide alcohols, the method illustrated in Example 3 can be used. In that method the tetrapeptide resin is treated with a swelling agent such as tetrahydrofuran. The swelled peptide resin is then reduced by treatment with a metal borohydride, preferably an alkali metal borohydride, such as $LiBH_4$ to provide the peptide alcohol. Reduction with alkali metal borohydride advantageously removes the bromocarbobenzoxy blocking group on the tyrosine simultaneous with reduction.

The tetrapeptides of this invention are useful by virtue of their narcotic agonist activity. Such agonists find use as analgesics, anti-depressant, anti-psychotic, anti-tussives and anti-diarrheal agents.

The compounds of Formula (I) may be combined with various typical pharmaeutical carriers to provide compositions suitable for use as analgesics, as anti-diarrheals and the like. The dosage of these compounds is dependent upon various factors, such as the particular compound employed and the particular response obtained.

The following examples describe in detail the preparation of compounds illustrative of the present invention. It will be apparent to those skilled in the art that many modifications, both of materials and methods, may be practiced without departing from the purpose and intent of this disclosure. Throughout the examples hereinafter set forth, temperatures are given in degrees Centigrade (°C.) and relative amounts in parts by weight, except as otherwise noted.

EXAMPLE 1

Synthesis of H-Tyr-DAla-Phe-Met-$NH_2$

The solid phase method was used in the standard way for the synthesis of peptides, using a Beckman 990 synthesizer. Boc amino acids were purchased from Beckman or Bachem Inc. The o-bromocarbobenzoxy (BrZ) protecting group was used for tyrosine side chain protection. Benzhydrylamine resin (0.54 eq/N/g, 1% crosslinked, Beckman) was reacted with Boc-methionine initially to obtain a yield of 0.385 mmole Boc-amino acid per g of resin. The resin was then acetylated with acetic anhydride and subsequent Boc-amino acids coupled in the usual fashion. At the completion of the last cycle, the peptide was cleaved from the resin and completely deprotected by treatment with anhydrous liquid HF at 0° for 45 min in the presence of anisole (10 ml HF and 1 ml anisole per gram resin). After removal of HF, the peptide was extracted with glacial acetic acid and the extract lyophilized. The crude peptide was purified by countercurrent distribution in n-butanol: acetic acid:water (nBAW) 4:1:5 for 100 transfers with subsequent cuts made for purity rather than yield; k=1.78.

TLC (silica gel, nBAW 12:3:5) $R_f$=0.62, single spot, Ninhydrin+, Pauly+, HVE: pH 2.8 (1 M HOAc) for 60 min at 1 KV, $E_{lys}$=0.47, single spot, Ninhydrin+, Pauly+, Amino acid analysis: Tyr, 1.02; Ala, 1.01; Phe, 1.02; Met, 0.95; 1.18 μm peptide/mg (62.5% peptide).

EXAMPLE 1A

Alternate Synthesis of H-Tyr-DAla-Phe-Met-NH$_2$

Step A: Preparation of Boc-Phe-Met-OCH$_3$

To a stirred solution of 10.97 g of Boc-Phe-OH and 5.72 g of N-hydroxysuccinimide (HOSu) in 50 ml of dimethylformamide (DMF) was added 8.54 g of dicyclohexylcarbodiimide (DCC). After 1 hour at 0° C., to mixture was allowed to warm to room temperature (1 hour). The resulting suspension was filtered (dicyclohexylurea removed) into a stirred solution of 7.52 g of Met-OCH$_3$.HCl and 7.12 ml of diisopropylethylamine (DIEA) in 50 ml of DMF. Two additional 3.56 ml portions of DIEA were added at 15 min intervals. Evaporation of the reaction mixture gave a residue which was dissolved in 300 ml of ethyl acetate (EtOAc) and washed with 1 N citric acid (4×50 ml), water (50 ml), 10% aqueous K$_2$CO$_3$ (4×40 ml), and saturated NaCl (50 ml). Evaporation of the dried (MgSO$_4$) EtOAc solution gave a syrup which was dissolved in 50 ml of EtOAc and diluted with 400 ml of hexane to give 13.1 g (85%) of Boc-Phe-Met-OCH$_3$, m.p. 91.5°–92.5° C., $[\alpha]_D^{21} = -19.24°$ (c, 1.7 in methanol).

Step B: Preparation of Boc-DAla-Phe-Met-OCH$_3$

To an ice cold solution of 16.42 g of Boc-Phe-Met-OCH$_3$ and 21.7 ml of anisole in 200 ml of EtOAc was introduced hydrogen chloride for 30 min. Evaporation of the solution gave a residue which was dissolved in 100 ml of EtOAc and diluted with 400 ml of hexane to give H-Phe-Met-OCH$_3$.HCl which was used without further purification.

In an analogous fashion as described in Step A, 7.56 g of Boc-DAla-OH, 5.06 g of HOSu, 8.25 g of DCC, 13.8 ml of DIEA and the HCl salt above were allowed to react in 100 ml of DMF to give 16.67 g (87% of Boc-DAla-Phe-Met-OCH$_3$, m.p. 109°–110° C., $[\alpha]_D^{24.5} = -19.73°$ (c, 1.00 in methanol).

Step C: Preparation of Boc-Tyr-DAla-Phe-Met-OCH$_3$

Boc-DAla-Phe-Met-OCH$_3$(9.4 g) was treated with HCl/anisole/EtOAc as described in Step B to give H-DAla-Phe-Met-OCH$_3$.HCl which was used without further purification.

In an analogous fashion as described in Step A except that the K$_2$CO$_3$ extraction was replaced with 1 N NaHCO$_3$, 4.58 g of Boc-Tyr-OH, 2.24 g of HOSu, 4.02 g of DCC, 6.7 ml of DIEA and the HCl salt above were allowed to react in 75 ml of DMF to give 10.85 g (80%) of Boc-Tyr-DAla-Phe-Met-OCH$_3$, m.p. 174°–175° C., $[\alpha]_D^{24.5} = -4.26°$ (c, 0.98 in methanol).

Step D: Preparation of Boc-Tyr-DAla-Phe-Met-NH$_2$

Boc-Tyr-DAla-Phe-Met-OCH$_3$ (2.33 g) was dissolved in 200 ml of methanol and the solution was saturated with ammonia at 0° C. After stirring the mixture in a pressure bottle at room temperature for 3 days, the solvent was evaporated and the residue dissolved in 200 ml of n-butanol. Washing of the butanol solution with 1 N HCl (50 ml), 1 N NaHCO$_3$ (3×50 ml), and water (4×50 ml) gave a residue on evaporation which was crystallized from EtOAc: hexane to give 2.21 g (97%) of Boc-Tyr-DAla-Phe-Met-NH$_2$ which was used directly in the next step without further purification.

Step E: Preparation of H-Tyr-DAla-Phe-Met-NH$_2$

A solution of 2.2 g of Boc-Tyr-DAla-Phe-Met-NH$_2$ in 20 ml of 10% anisole in trifluoroacetic acid (TFA) was stirred for 30 min. Evaporation of the solvent gave a residue which was dissolved in 20 ml of water:methanol:acetic acid (94:5:1) and applied to a column of Amberlite XAD-2 (44–74 μm, 2.7×60 cm). The sample was eluted at 6 ml/min with a convex gradient formed from 2 L of water:methanol:acetic acid (94:5:1) into which was fed methanol:water:acetic acid (50:49:1). Evaporation of the product peak gave a syrup which was dissolved in 100 ml of ethanol and diluted with 100 ml of ether to give 1.37 g (66%) of H-Tyr-DAla-Phe-Met-NH$_2$.HOAc, m.p. 210°–211° C., $[\alpha]_D^{25} = 45.21°$ (c, 1.00 in 10% acetic acid).

EXAMPLE 2

Synthesis of H-Tyr-DLys-Phe-Met-NH$_2$

This peptide was synthesized on benzyhydrylamine resin in exactly the same manner as described in Example 1, substituting DLys for DAla at position 2. The epsilon amino group of lysine was blocked by the 2-chlorocarbobenzoxy group during synthesis. After cleavage of the resin with HF, extraction with glacial HOAc and lyophilization, the crude peptide was purified by countercurrent distribution in nBAW 4:1:5, for 100 transfers; k=0.282. TLC (silica gel): nBAW 12:3:5, R$_f$=0.33, Ninhydrin+, Pauly+, HVE (pH 2.8, 60 min at 1 KV): E$_{lys}$=0.784, single spot, Ninhydrin+, Pauly+, Amino acid analysis: Tyr, 0.96, Lys, 1.04; Phe, 1.02; Met, 0.98. 1.24 μm peptide/mg; 72.6% peptide.

EXAMPLE 3

Synthesis of H-Tyr-DAla-Phe-Methioninol

Boc-methionine was esterified to hydroxymethylpolystyrene-divinylbenzene (1% crosslinked) using dicyclohexylcarbodiimide and a p-dimethylaminopyridine catalyst; amino acid analysis showed a substitution of 0.316 mmoles Met/g resin. Excess hydroxyl groups were acetylated, and the peptide was assembled on the resin in the standard fashion, using the Beckman 990 synthesizer. The hydroxyl group of tyrosine was blocked during synthesis with the bromocarbobenzoxy group. Next, 2 g of peptide resin, H-Tyr(Brz)-DAla-Phe-Met-OCH$_2$-resin, was placed into a 100 ml round-bottomed flask. Then, 133 mg LiBH$_4$(ALFA) (about 10 equiv. excess over resin substitution value for Met) dissolved in 75 ml tetrahydrofuran (THF, peroxidefree) was added. A drying tube was placed on the flask and the reaction mixture stirred at room temperature for 2 hours. Excess LiBH$_4$ was destroyed with glacial HOAc and the mixture then filtered through a coarse sintered-glass funnel. After several washes of resin with glacial HOAc, the solvents were evaporated under reduced pressure and freeze-dried. The crude lyophilized peptide (Pauly+) and remaining Li salts were then subjected to countercurrent distribution in nBAW, 4:1:5, for 100 transfers. CCD cuts were made to maximize purity rather than yield. Some 355 mg peptide was recovered from the various cuts and all cuts contained the same major product in excess over any impurities. A particularly homogeneous cut, k=2.70, yielded 55 mg of essentially pure peptide, H-Tyr-DAla-Phe-Met-ol. (TLC: nBAW 12:3:5, silica gel, R$_f$=0.70, Nin+, Pauly+; HVE: 1 M HOAc, pH 2.8, 60 min at 1 KV, E$_{lys}$=0.44, Nin+, Pauly+; amino acid analysis: Tyr, 0.99; Ala, 1.01; Phe, 1.01; Met, 0.0; Met-ol was not detectable on analyzer).

EXAMPLE 3A

Alternate Synthesis of H-Tyr-DAla-Phe-Methioninol

Step A: Preparation of Boc-Tyr-DAla-Phe-Methioninol

To a solution of Boc-Tyr-DAla-Phe-Met-OCH$_3$ (5.8 g) (prepared in Step C of Example 1A) in 100 ml of dry tetrahydrofuran under nitrogen was added 1.0 g of LiBH$_4$. After stirring at room temperature for 1 hour, 6 ml of acetic acid was added slowly followed by 50 ml of methanol to destroy excess LiBH$_4$. Evaporation of the solution gave an oil which was dissolved in 250 ml of EtOAc and washed with 1 N HCl (4×25 ml), 1 N NaHCO$_3$ (3×50 ml) and saturated NaCl (3×50 ml). Evaporation of the MgSO$_4$ dried EtOAc solution gave a foam which was dissolved in 25 ml of hot EtOAc and diluted with 100 ml of hexane to give a solid. The solid was recrystallized from 50 ml of isopropanol and 100 ml of water to give 5.7 g (93%) of Boc-Tyr-DAla-Phe-Methioninol, m.p. 107–100° C., $[\alpha]_D^{25} = 0.08°$ (c, 1.00 in methanol).

Step B: Preparation of H-Tyr-DAla-Phe-Methioninol

A solution of 2.47 g of Boc-Tyr-DAla-Phe-Methioninol in 20 ml of 10% anisole in TFA was stirred for 30 min and then evaporated to a syrup. The syrup was dissolved in 20 ml of methanol, water, acetic acid (50:49:1) and applied to an Amberlite XAD-2 column (44–74 μm, 2.7×60 cm). Elution of the sample at 5 ml/min with a linear gradient formed from 2 liters each of water:methanol:acetic acid (94:5:1) to methanol:water:acetic acid (94:5:1) gave a product peak which was evaporated to a syrup. The syrup was dissolved in 20 ml of isopropanol and diluted with 150 ml of ether to give 1.85 g (82%) of H-Tyr-DAla-Phe-Methioninol·HOAc, m.p. 110°–120° C., $[\alpha]_D^{25} = 24.05°$ (C, 0.98, methanol).

EXAMPLE 4

Synthesis of H-Tyr-DAla-Phe-Met-OCH$_3$

As in step A of Example 1A, 2.0 g of Boc-Tyr-DAla-Phe-Met-OCH$_3$ was treated with HCl, anisole, EtOAC to give H-Tyr-DAla-Phe-Met-OCH$_3$.HCl which was dissolved in 40 ml of water, methanol, acetic acid (94:5:1) and applied to a column (2.5×100 cm) of C$_{18}$Hi+Flosil (80–100 mesh, Applied Science Laboratories, Inc.). The sample was eluted at 3 ml/min with a convex gradient formed from 2 liters of water, methanol, acetic acid (94:5:1) into which was fed methanol, water, acetic acid (50:49:1). The solid resulting from the evaporation of the product peak was dissolved in 10 ml of isopropanol and diluted with 100 ml of hexane to give 1.27 g (68%) of H-Tyr-DAla-Phe-Met-OCH$_3$.HOAc, m.p. 64°–65° C., $[\alpha]_D^{26} = 10.57°$, (c, 1.01 in methanol).

EXAMPLE 5

Synthesis of H-Tyr-DAla-Phe-Met-OH

Step A: Preparation of Boc-Tyr-DAla-Phe-Met-OH

To a stirred solution of 2.0 g of Boc-Tyr-DAla-Phe-Met-OCH$_3$ (prepared as in Step C of Example 1A) in 50 ml of methanol was added 8.0 ml of 1 N NaOH. Evaporation of the solution after stirring at room temperature for 1 hour gave a residue which was dissolved in 30 ml of EtOAc and washed with 1 N HCl (4×50 ml) and saturated NaCl (3×50 ml). The MgSO$_4$ dried EtOAc solution was evaporated to a residue which was purified by chromatography on silica gel with a gradient of chloroform to 10% acetic acid in chloroform to give 1.12 g (57%) of Boc-Tyr-DAla-Phe-Met-OH, m.p. 135° C.

Step B: Preparation of H-Tyr-DAla-Phe-Met-OH

In a fashion analogous to Step B of Example 3A, 1.1 g of Boc-Tyr-DAla-Phe-Met-OH was treated with 10% anisole in TFA and chromatographed on Amberlite XAD-2 to give 0.64 g (60%) of H-Tyr-DAla-Phe-Met-OH, m.p. 248°–249° C., $[\alpha]_D^{25.5} = 41.06°$ (c, 1.00 in 50% acetic acid).

EXAMPLE 6

Preparation of H-Tyr-DAla-Phe-Met-NHCH$_2$CH$_3$

Step A: Preparation of Boc-Tyr-DAla-Phe-Met-NHCH$_2$CH$_3$

In a fashion analogous to Step D of Example 1A, 2.15 g of Boc-Tyr-DAla-Phe-Met-OCH$_3$ was treated with 20 ml of ethylamine in 200 ml of methanol to give 2.01 g (92%) of Boc-Tyr-DAla-Phe-Met-NHCH$_2$CH$_3$, m.p. 159°–161° C., $[\alpha]_D^{25} = 5.04°$ (c, 0.97 in methanol).

Step B: Preparation of H-Tyr-DAla-Phe-Met-NHCH$_2$CH$_3$

In a fashion analogous to Example 4, 1.64 g of Boc-Tyr-DAla-Phe-Met-NHCH$_2$C$_3$ was treated with HCl, anisole, EtOAC and chromatographed on C$_{18}$Hi+-Flosil to give 0.82 g (53%) of H-Tyr-DAla-Phe-Met-NHCH$_2$CH$_3$.HOAc, m.p. 170°–175° C., $[\alpha]_D^{26} = 5.24°$ (c, 1.0 in methanol).

EXAMPLE 7

Synthesis of H-Tyr-DAla-Phe-Met-NHCH$_2$CH$_2$OH

Step A: Preparation of Boc-Tyr-Dala-Phe-Met-NHCH$_2$CH$_2$OH

In a fashion analogous to Step D of Example 1A, 2.15 g of Boc-Tyr-DAla-Phe-Met-OCH$_3$ was treated with 20 ml of 2-aminoethanol in 200 ml of methanol to give 2.15 g (97%) of Boc-Tyr-DAla-Phe-Met-NHCH$_2$CH$_2$OH, m.p. 145°–150° C., $[\alpha]_D^{24.5} = 0.36°$ (c, 1.00 in methanol).

Step B: Preparation of H-Tyr-DAla-Phe-Met-NHCH$_2$CH$_2$OH

Boc-Tyr-DAla-Phe-Met-NHCH$_2$CH$_2$OH (2.0 g) was treated with HCl, anisole, EtOAc as in Step B to give H-Tyr-DAla-Phe-Met-NHCH$_2$CH$_2$OH.HCl which was chromatographed on Amberlite XAD-2 as in Step E to give 1.23 g (64%) of H-Tyr-DAla-Phe-Met-NHCH$_2$CH$_2$OH.HOAc, m.p. 200°–203° C., $[\alpha]_D^{26} = 10.21°$ (c, 1.01 in methanol).

EXAMPLE 8

Synthesis of H-Tyr-DAla-Phe-Met(O)-ol

Step A: Preparation of Boc-Tyr-DAla-Phe-Met(O)-ol

To a solution of 2.47 g of Boc-Tyr-DAla-Phe-Met-(O)-ol in 35 ml of 90% acetic acid was added 0.6 ml of 30% hydrogen peroxide. After 1 hr, the solution was evaporated to a syrup which was chromatographed on silica gel in methylene chloride:methanol:acetic acid:water (180:14:3:3) to give a product peak which was evaporated to a solid which was crystallized from 30 ml of EtOAc and 60 ml of hexane to give 2.02 g (80%) of Boc-Tyr-DAla-Phe-Met(O)-ol, m.p. 163°–167° C., $[\alpha]_D^{25} = 7.41°$ (c, 0.97 in methanol).

Step B: Preparation of H-Tyr-DAla-Phe-Met(O)=ol

In a fashion analogous to Step B, Example 5, 1.9 g of Boc-Tyr-DAla-Phe-Met(O)-ol was treated with 10% anisole in TFA and chromatographed on Amberlite XAD-2 to give 1.4 g (79%) of H-Tyr-DAla-Phe-Methioninol sulfoxide, m.p. 140°-155°, $[\alpha]_D^{25}=19.00°$ (c, 1.06 in methanol).

EXAMPLE 9

Synthesis of H-Tyr-DAla-Phe-Leu-NH₂

Boc-leucine was esterified to chloromethyl polystyrene-1% divinylbenzene in the standard way (cf. Stewart and Young) to give a product containing 0.347 mmoles leucine per gram resin. The peptide sequence was assembled on the resin in the standard way described for Example 1 above, using the Beckman 990 synthesizer. H-Tyr(BrZ)-DAla-Phe-Leu-resin was suspended in anhydrous methanol in a pressure vessel. The solution was chilled to −20°, saturated with ammonia gas, and the vessel was closed and stirred at room temperature for 2 days. Excess ammonia was removed under reduced pressure, the resin was filtered off and discarded, and the peptide solution evaporated to dryness. The blocking group was removed from the tyrosine by treatment with HF-anisole as described in Example 1 above. The peptide was purified by CCD in nBAW (4:1:5); the partition coefficient was 3.0. On paper electrophoresis at pH 5.0 the peptide had $E_{lys}=0.50$.

EXAMPLE 10

The tetrapeptides prepared in Examples 1–9 were evaluated for their activity in vitro on stimulated guinea pig ileum strips according to the method described by S. Ehrenpries and A. Neidle, in *Methods in Narcotic Research*, Ed. (Marcel Dekker, Inc., New York, 1975) p. 111.

Male Hartley guinea pigs (Dutchland, Inc.), N=3/drug, were killed by a blow to the head and 3–4 cm long strips of intact ileum were removed from a section of gut approximately 10 cm proximal to the caecum. The muscle was placed in a 10 ml tissue bath containing Tyrode's solution maintained at 37°±1° and bubbled with 98% O₂:2% CO₂.

The ileum was stimulated by a Grass model S4K stimulator at the following parameters: 100 volts potential, 0.2 Hz frequency and 0.4 msec. duration. Contractions were recorded by a Grass polygraph via a Grass model FT03 transducer. Peptides were usually added to the bath in volumes no greater than 100 μl. Occasionally as much as 500 μl was added. All doses were separated by at least 8–10 min. All peptides were dissolved in Tyrode's solution.

The molar concentration of peptide which reduces the contractions to 50% of the control was defined as the ED₅₀ concentration. The results obtained are summarized in Table 1.

TABLE 1

| Example | Structure | ED₅₀ |
|---|---|---|
| 1 | H—Tyr—DAla—Phe—Met—NH₂ | $1.4 \times 10^{-8}$ |
| 2 | H—Tyr—DLys—Phe—Met—NH₂ | $3.6 \times 10^{-7}$ |
| 3 | H—Tyr—DAla—Phe—Met—ol | $4.2 \times 10^{-8}$ |

TABLE 1-continued

| Example | Structure | ED₅₀ |
|---|---|---|
| 4 | H—Tyr—DAla—Phe—Met—OCH₃ | $6.2 \times 10^{-8}$ |
| 5 | H—Tyr—DAla—Phe—Met—OH | $1.4 \times 10^{-6}$ |
| 6 | H—Tyr—DAla—Phe—Met—NH—CH₂—CH₃ | $1.2 \times 10^{-7}$ |
| 7 | H—Tyr—DAla—Phe—Met—NH—(CH₂)₂OH | $1.9 \times 10^{-7}$ |
| 8 | H—Tyr—DAla—Phe—Met(O)—ol | $1.4 \times 10^{-7}$ |
| 9 | H—Tyr—DAla—Phe—Leu—NH₂ | $2.0 \times 10^{-8}$ |
| Standard | H—Tyr—Gly—Gly—Phe—Met—OH | $1.1 \times 10^{-8}$ |

We claim:

1. Tetrapeptides having the formula

H-Tyr-X-Y-Z wherein
X is a D-amino acid radical selected from the group consisting of D-Ala and D-Lys;
Y is Phe, DPhe, MePhe, DMePhe, Trp or DTrp;
Z is Met-OH, Met-ol, Met(O)-ol, Met-OR, Met-NH₂, Met-NHR, DMet-OH, DMet-ol, DMet(O)-ol, DMet-OR, DMet-NH₂, DMet-NHR, Leu-OH, Leu-ol, Leu-OR, Leu-NH₂, Leu-NHR, DLeu-OH, DLeu-ol, DLeu-OR, DLeu-NH₂, or DLeu-NHR; and
R is C₁–C₄-alkyl or C₁–C₄-hydroxyalkyl.

2. The tetrapeptide of claim 1 wherein
X is DAla or DLys;
Y is Phe or DPhe; and
Z is Met-OH, Met-NH₂, -Met-ol, Met-OCH₃, Met-NHCH₃, Met-NHC₂H₅, Met-NH-(CH₂)₂-OH, Met-(O)-ol or Leu-NH₂.

3. The tetrapeptide of claim 1 having the formula

H-Tyr-DAla-Phe-Met-NH₂.

4. The tetrapeptide of claim 1 having the formula

H-Tyr-DLys-Phe-Met-NH₂.

5. The tetrapeptide of claim 1 having the formula

H-Tyr-DAla-Phe-Met-ol.

6. The tetrapeptide of claim 1 having the formula

H-Tyr-DAla-Phe-Met-OCH₃.

7. The tetrapeptide of claim 1 having the formula

H-Tyr-DAla-Phe-Met-OH.

8. The tetrapeptide of claim 1 having the formula

H-Tyr-DAla-Phe-Met-NH-CH₂-CH₃.

9. The tetrapeptide of claim 1 having the formula

H-Tyr-DAla-Phe-Met-NH-(CH₂)₂-OH.

10. The tetrapeptide of claim 1 having the formula

H-Tyr-DAla-Phe-Met(O)-ol.

11. The tetrapeptide of claim 1 having the formula

H-Tyr-DAla-Phe-Leu-NH₂.

* * * * *